United States Patent [19]

Kelkenberg

[11] Patent Number: 5,496,933
[45] Date of Patent: Mar. 5, 1996

[54] SUPER-ABSORBENTS AND A PROCESS FOR THEIR PREPARATION

[75] Inventor: Heike Kelkenberg, Gladbeck, Germany

[73] Assignee: Chemische Fabrik Stockhausen GmbH, Krefeld, Germany

[21] Appl. No.: 243,791

[22] Filed: May 17, 1994

[30] Foreign Application Priority Data

Jun. 1, 1993 [DE] Germany ............... 43 18 094.9

[51] Int. Cl.⁶ ............... C08B 37/08; C07C 17/00; C07H 1/00
[52] U.S. Cl. ............... 536/20; 536/124; 536/127; 525/54.3; 604/358; 604/367; 604/374; 604/375; 604/376
[58] Field of Search ............... 536/20, 124, 127; 525/54.3; 604/358, 367, 374, 375, 376, 377

[56] References Cited

U.S. PATENT DOCUMENTS

| | | | |
|---|---|---|---|
| 4,929,722 | 5/1990 | Partin, III et al. | 536/20 |
| 4,975,542 | 12/1990 | Hirayama et al. | 536/20 |
| 5,322,935 | 6/1994 | Smith | 536/20 |

FOREIGN PATENT DOCUMENTS

| | | |
|---|---|---|
| 0212688 | 3/1987 | European Pat. Off. . |
| 0424672 | 5/1991 | European Pat. Off. . |
| WO90/10426 | 9/1990 | WIPO . |

OTHER PUBLICATIONS

Database WPI, Derwent Publications Ltd., AN 87-120043, JP-A-62 064 803, Mar. 23, 1987.

Primary Examiner—Nathan M. Nutter
Attorney, Agent, or Firm—Oblon, Spivak, McClelland, Maier & Neustadt

[57] ABSTRACT

Chitosan absorbent is prepared by reacting pulverized chitosan suspended as a powder in an organic solvent with an acid and then isolating solid chitosan-acid reaction product.

12 Claims, No Drawings

SUPER-ABSORBENTS AND A PROCESS FOR THEIR PREPARATION

BACKGROUND OF THE INVENTION

1. Field of the Invention

The present invention relates to super-absorbents, to a process for their preparation and to their use in the hygiene sector.

2. Discussion of the Background

Super-absorbents, or highly water-absorbent and water-swellable polymers, are widely used in the sanitary and hygiene sector, in wallpaper pastes, as drying agents, as humectants in agriculture and as electrolyte thickeners in dry batteries. Known absorbents for these intended uses include synthetic polymers or starch graft polymers or cellulose graft polymers, the hydrophilicity of which is based on a high content of carboxyl groups. The fully synthetic polymers are usually polymers with a low degree of crosslinking such as partly crosslinked polyacrylic acid salts or partly crosslinked polymaleic acid derivatives. They have comparatively the best absorbent action, but are not degraded biologically.

Suitable graft polymers are derivatized polysaccharides in which water-soluble vinyl monomers are usually grafted therein. The graft polymers include the carboxymethyl cellulose, hydrolyzed starch/acrylonitrile graft polymers and acrylic acid/starch graft polymers. In comparison with the fully synthetic polymers, they display a significantly lower absorption capacity for water and aqueous liquids. However, the proportional biological degradation of these naturally occurring swelling agents is advantageous. Nevertheless, the preparation of such graft polymers is very expensive and the amount of biopolymer in the end product is severely limited by the high viscosity of the reaction medium, as is the case, for example, of a monomer solution of dissolved starch. Reference may be made in this respect, for example, to EP-A-0 168 390 and EP-A-0 188 489.

It is known from DE-A-35 05 920 that polymers or copolymers having a low degree of crosslinking, the hydrophilicity of which is based on a high content of cationic groups, are preferable to known anionic absorbents. In particular, they are less sensitive to salt solutions and display a significantly better absorption capacity. Suitable cationic absorbents are, inter alia, copolymers based on quaternary ammonium compounds and acrylamide, which can be polymerized by free radicals. These fully synthetic cationic polymers, like the fully synthetic anionic polymers, are not biologically degradable. A need therefore continues to exist for a biodegradable material of high absorbing capacity.

SUMMARY OF THE INVENTION

Accordingly, one object of the present invention is to provide biologically degradable cationic absorbents which are based on naturally occurring biopolymers.

Briefly, this object and other objects of the present invention as hereinafter will become more readily apparent can be attained by a method for preparing chitosan salts by reacting pulverized chitosan suspended as a powder in an organic solvent with an acid, and then isolating the solid chitosan-acid reaction product. The chitosan salts have a high absorption rate and absorption capacity.

DESCRIPTION OF THE PREFERRED EMBODIMENTS

The chitosan salt product of the present invention preferably comprise 1 to 30, in particular 2 to 10 mmol of acid per gram of chitosan. The chitosan salts are preferably crosslinked with the aid of a crosslinking agent. They then comprise, in general, 0.0001 to 10 mmol of crosslinking agent per gram of chitosan.

Another aspect of the invention is a process for the preparation of super-absorbents based on chitosan. The chitosan salts are obtained by reacting pulverized chitosan with an acid in an organic solvent. The abovementioned amounts of acid are preferably used in the reaction. The products can be crosslinked with a crosslinking agent during the reaction with the acid or thereafter. Preferably, 0.0001 to 10 mmol of crosslinking agent are used per gram of chitosan. After grinding, the chitosan is pulverized with particle sizes of ≦1 mm. However, the powder employed in general has less than 10% by weight of particles with particle sizes of <1 µm.

Chemically, chitosan is a polysaccharide which contains amino groups and has a linear structure analogous to that of cellulose.

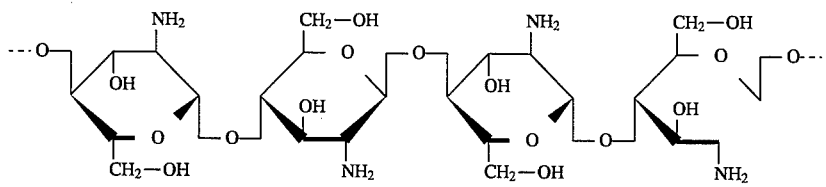

Structure of Chitosan (section)

In recent years, chitosan has gained economic importance as a renewable biological raw material chiefly in Japan and the USA. It is produced by deacetylation of chitin, a waste product of the crab industry. After cellulose, chitin is the second most common polysaccharide on earth. Commercially available chitosan still contains about 20% of acetylated amino groups, has a molecular weight of 300,000 to 500,000 and is insoluble in most organic solvents and in water. In contrast, chitosan is soluble in dilute acids. Because of the high molecular weight of chitosan, these solutions are very highly viscous, so that reactions can be carried out only in a very high dilution. Working up of such solutions is a major problem industrially. It is therefore surprising that chitosan can be reacted with acids in a heterogeneous phase system, suspended as a powder in an organic solvent. The characteristic of the powder is retained. The product can be handled as a solid.

Suitable organic solvents for the process include alcohols such as, for example, methanol, ethanol, propanol isopropanol, butanol, pentanol, cyclohexanol, and the like etc. In addition, however, it is also possible to use ketones such as, for example, acetone, methyl ethyl ketone, methyl isobutyl ketone and diisobutyl ketone. Esters, such as, for example, methyl acetate or ethyl acetate, can also be employed. Solvents in which the acid to be reacted is soluble are most suitable. Furthermore, solvents which are capable of dissolving small amounts of water are preferred. Preferred solvents are methanol, ethanol, acetone and butanol. Solvent mixtures can also be used.

The commercially available chitosan should be employed as far as possible in the ground state with a particle size of $\leq 500$ μm. Nevertheless, even chitosan which has not been treated industrially is correspondingly reactive. The ratio of chitosan to solvent can be varied and depends on the reaction vessel used. However, the suspension should not be too dilute, in order to ensure as complete as possible a conversion of the acid.

The weight ratio of the solvent to chitosan is usually in the range from 1:1 to 100:1, preferably 5:1 to 20:1. At a ratio of 1:1, the mixture can be reacted with an acid in the kneader or in an extruder. A mixing ratio of 10:1 is preferably used in a customary stirred reactor.

The reaction is preferably carried out in the presence of a low content of water. The amount of water usually ranges from 1 to 200%, preferably 1 to 80%, based on the chitosan employed. The chitosan suspended in the organic phase is initially swollen somewhat by the water. The reaction with the acid is usually carried out in the temperature range from 15° to 150° C. Temperatures of 40° to 90° C. are preferred here. While up to 30 hours is sometimes necessary at room temperature, the reaction can in general be carried out in the course of 1 to 8 hours in the preferred temperature range or at the boiling point of the solvent.

Either inorganic or organic acids can be reacted with chitosan in the suspension. Strong acids are preferably employed here. Suitable acids are, for example, mineral acids, sulfonic acids, carboxylic acids having 1 to 4 carboxyl groups and hydroxycarboxylic acids. Mixtures of acids can also be used. Reaction products having very different properties are obtained, depending on the acid. For example, a product which is soluble in cold water in powder form and has an astonishingly low viscosity as a solution is obtained with hydrochloric acid. On the other hand, the products with sulfuric acid and phosphoric acid are water-insoluble products, which can possibly be explained by crosslinking of the salt. Formic acid gives a reaction product which is soluble in water to give a cloudy solution and has a high viscosity. The hydroxy acids, such as for example, lactic acid and glycolic acid, show a surprising result. With these, the chitosan salts form glass-clear gels in water. Organic acids, and in particular hydroxy acids, are preferably used for the super-absorbents.

The swellability of the chitosan salts can be improved further by after-crosslinking. Suitable crosslinking agents include all the polyfunctional substances which are capable of reacting with amino or OH groups, and the number of functional groups should preferably be two. Examples of crosslinking agents in the context of the invention include dicarboxylic acids, dianhydrides, dicarboxylic acid chlorides, diepoxides and dialdehydes. The crosslinking agents are preferably selected so that the crosslinking sites formed can easily be reopened biologically or hydrolytically in order to ensure the desired biodegradation.

Since the chitosan salts are very long polymer chains, only a very small amount of crosslinker component is necessary to achieve optimum crosslinking. If the degree of crosslinking is too high, the swellability is adversely influenced and decreases significantly. The amount of crosslinking agent added depends on its nature. In the case of dicarboxylic acids, dianhydrides and diacid chlorides, a comparatively large amount of crosslinking agent of 0.01 to 10 mmol/g of chitosan must be employed, since these crosslinking agents can react partly with the water, which is preferably present in small amounts, or with the alcohols, if these have been used as solvents. On the other hand, diepoxides and dialdehydes react preferentially with the amino groups of the chitosan salt, so that these are used, for example, in amounts of only $10^{-4}$ to $10^{-2}$ mmol/g of chitosan.

In the case where dialdehydes are used as crosslinking agents, aldimine bonds are formed as crosslinker sites with the amino groups of the chitosan salt, and are easily split open again hydrolytically by water in the waste water or otherwise in the environment and are therefore readily biologically degradable. In comparison with the dialdehyde-crosslinked products, the epoxide-crosslinked products show a slightly delayed biological degradation. The water absorption capacity of chitosan-lactic acid and chitosan-glyoxylic acid is significantly increased, for example, by subsequent crosslinking. The biologically degradable products according to the invention show a good absorption capacity in particular with respect to synthetic urine. They are therefore particularly suitable for incorporation into environmentally friendly cellulose-containing absorbent hygiene articles, such as disposable napkins, sanitary towels, dish cloths and hospital underblankets. They can furthermore be used in wallpaper pastes, as drying agents and as water reservoirs or humectants in agriculture and in cosmetic and pharmaceutical products.

Having generally described this invention, a further understanding can be obtained by reference to certain specific examples which are provided herein for purposes of illustration only and are not intended to be limiting unless otherwise specified.

The following determination methods are used to characterize the liquid absorption capacity and the biological degradability:

Absorption Value

About 0.5 g of product is sprinkled onto a glass frit (type G3, diameter 50 mm) which is connected to a burette filled with completely demineralized water or synthetic urine and levelled at the level of the glass frit. The amount of liquid absorbed is measured on the burette after 0.5 and 10 minutes.

$$\text{Absorption value} = \frac{\text{amount of liquid absorbed}}{\text{weight}} \text{ (ml/g)}$$

The initial value after 0.5 minute is a measure of the absorption rate. The final value after 10 minutes is a measure of the absorption capacity.

Composition of the Synthetic Urine 970.77 g of completely demineralized water 8.30 g of sodium chloride 0.60 g of calcium chloride 0.93 g of magnesium sulfate with 6 molecules of water of crystallization.

19.40 g of urea.

Biological Degradation

Biological degradation is investigated by the so-called modified Sturm test in accordance with the OECD standard (301 B adopted: 12.05.81).

A 2.5 l amount of nutrient solution is introduced into a 5 l vessel and 30 ml of sewage sludge (supernatant) from a municipal sewage plant are added. This mixture is gassed with $CO_2$-free air for 24 hours. Three absorption vessels each containing 100 ml of 0.025M NaOH are then connected in series after the 5 l vessel. After addition of 60 ml of an aqueous 0.1% strength solution of the substance to be tested, the flask is filled up to 3 l with 413 ml of completely demineralized water (sodium benzoate is used as the control substance).

Nutrient Salt Content
- 22.50 mg/l of $MgSO_4 \times 7 \cdot H_2O$
- 40.00 mg/l of $(NH_4)_2SO_4$
- 27.50 mg/l of $CaCl_2$ (anhydrous)
- 1.00 mg/l of $FeCl_3 \times 6 \cdot H_2O$
- 17.00 mg/l of $KH_2PO_4$; 43.5 mg/l of $K_2HPO_4$
- 66.80 mg/l of $Na_2HPO_4 \times 7 \cdot H_2O$
- 3.40 mg/l of $NH_4Cl$ The vessel is gassed with 50 to 100 ml/min of $CO_2$-free air, the $CO_2$ formed by the biological degradation being retained as $Na_2CO_3$ in the absorption vessels. The NaOH which remains is titrated potentiometrically with 0.05M HCl every second day within the first 10 days and then every fifth day. After the measurement, 1 ml of concentrated hydrochloric acid is added to liberate the $CO_2$ of the inorganic carbonate. The content of organically bonded carbon in the test substance serves as the reference parameter.

$$CO_2\text{-production} = [\text{ml of HCl (blank value)} - \text{ml of HCl (test)}] \times 1.10 \text{ mg}(CO_2)$$

$$\% \text{ biodegradation} = \frac{\text{mg } CO_2 \text{ produced}}{60 \text{ mg} \times CO_2 \text{ content (theoretical)}} \times 100$$

Having generally described this invention, a further understanding can be obtained by reference to certain specific examples which are provided herein for purposes of illustration only and are not intended to be limiting unless otherwise specified.

EXAMPLE 1

Chitosan HCl Salt

A 103 g amount of methanolic hydrochloric acid (corresponding to 80 mmol of HCl) and 10 g of water are initially introduced into a stirred flask in the cold, and 10 g of ground chitosan powder (<500 μm) are added, while stirring vigorously. Thereafter, the mixture is heated up to the reflux temperature. After a reaction time of 4 hours, the uptake of acid has ended. After cooling, the mixture is centrifuged and the residue is washed twice with methanol and dried to constant weight.
Weight: 11.7 g.

The powder is soluble in cold water. A 1% strength solution shows a viscosity no different than that of water.

EXAMPLE 2

Chitosan Formic Acid Salt

A 10 g amount of chitosan powder is reacted with 80 mmol of formic acid analogously to the procedure of Example 1.
Weight: 10.5 g.

The powder is soluble in cold water to give a cloudy solution. A 1% strength solution shows an increased viscosity.

EXAMPLE 3

Chitosan Glycolic Acid Salt

A 10 g amount of industrial chitosan in non-ground form is reacted with 80 mmol of glycolic acid analogously to the procedure of Example 1.
Weight: 13.6 g.

The powder is soluble in cold water to give a clear solution. A 1% strength solution is highly viscous and scarcely capable of flowing.

EXAMPLE 4

Chitosan-3-hydroxybutyric Acid Salt

A 10 g amount of ground chitosan powder is reacted with 80 mmol of 3-hydroxybutyric acid analogously to the procedure of Example 1.
Weight: 10.7 g.

The product initially swells slightly in cold water, but is insoluble.

EXAMPLE 5

Chitosan Lactic Acid Salt

A 10 g amount of ground chitosan powder is reacted with 80 mmol of lactic acid analogously to the procedure of Example 1.
Weight: 13.6 g The product swells severely in cold water. A 1% strength solution forms a clear gel which almost stands up.

EXAMPLE 6

Chitosan Lactic Acid Salt

A 100 g amount of ethanol, 7.4 g of water and 9.8 g of lactic acid are initially introduced into a reaction vessel, and a 10 g amount of ground chitosan powder is added, while stirring. Thereafter, the mixture is heated under reflux for 3 hours. After cooling, the content of the vessel is filtered and the residue on the filter is washed with ethanol and dried.
Weight: 13.1 g.

The product swells severely in cold water. A 1% strength solution is a clear mobile gel.

EXAMPLE 7

Chitosan Lactic Acid Salt

The preparation is carried out analogously to the procedure of Example 6, using acetone instead of ethanol as the solvent.
Weight: 13.5 g.

The product swells severely in cold water. A 1% strength solution is a clear mobile gel.

EXAMPLES 8 TO 21

Examples 8 to 21 (Table 1 below) describe chitosan lactic acid salts crosslinked with glutaraldehyde.

The crosslinking reaction is carried out in various solvents by the following method:

A 100 g amount of solvent and 10 g of water are initially introduced into the reaction vessel and a 13 g amount of chitosan lactic acid salt (Example 5) is added, while stirring. After a swelling time of 10 minutes, 3 ml of a 5 mmolar solution of glutaric dialdehyde in the solvent (=0.015 mmol) are slowly added dropwise, while stirring vigorously. Thereafter, the mixture is heated at 58° C. for 1 hour. After cooling, the content of the vessel is filtered and the filter cake is washed with a little solvent and dried at 50° C. in vacuo.

The absorption values of the crosslinked products prepared in various solvents are summarized in the following table.

TABLE 1

| Product crosslinked with glutaric dialdehyde | | Absorption value in completely demineralized water (ml/g) | |
|---|---|---|---|
| Example | Solvent | 0.5 minute | 10 minutes |
| 8 | Acetone | 42.9 | 83.0 |
| 9 | 1-butanol | 36.2 | 84.0 |
| 10 | Ethyl methyl ketone | 15.2 | 21.7 |
| 11 | Isopropanol | 33.7 | 68.6 |
| 12 | Cyclohexanol | 24.4 | 48.8 |
| 13 | 2-ethylhexan-1-ol | 21.3 | 45.7 |
| 14 | Methanol | 12.5 | 54.2 |
| 15 | Ethyl acetate | 14.3 | 19.4 |
| 16 | Methyl acetate | 28.1 | 78.1 |

Examples 17 to 21 describe crosslinked chitosan lactic acid salts which are prepared in acetone with various amounts of glutaric dialdehyde as the crosslinking agent.

TABLE 2

| Crosslinked product | | Absorption value in completely demineralized water (ml/g) | |
|---|---|---|---|
| | Glutaric dialdehyde | | |
| Example | (mmol/g of product) | 0.5 minute | 10 minutes |
| 17 | 0.00 | 35.6 | 70.2 |
| 18 | 0.0008 | 42.9 | 80.4 |
| 19 | 0.00115 | 42.9 | 83.0 |
| 20 | 0.0023 | 37.2 | 76.6 |
| 21 | 0.0307 | 28.0 | 68.0 |

EXAMPLES 22 TO 27

Examples 22 to 27 describe chitosan lactic acid salts crosslinked with sorbitol diglycidyl ether. The crosslinking reaction is carried out in various solvents by the following method:

A 100 g amount of solvent and 10 g of water are initially introduced into the reaction vessel, and 13 g of chitosan lactic acid salt (Example 5) are added, while stirring. After a swelling time of 10 minutes, 4 ml of a 5 mmolar solution of glutaric dialdehyde in the solvent (=0.02 mmol) are slowly added dropwise while stirring vigorously. Thereafter, the mixture is heated at 58° C. for 1 hour. After cooling, the mixture is filtered and the filter cake is washed with a little solvent and dried at 50° C. in vacuo.

The absorption values of the crosslinked products prepared in various solvents are summarized in Table 3.

TABLE 3

| Product crosslinked with sorbitol diglycidyl ether | | Absorption value in completely demineralized water (ml/g) | |
|---|---|---|---|
| Example | Solvent | 0.5 minute | 10 minutes |
| 22 | Acetone | 38.9 | 87.7 |
| 23 | 1-butanol | 31.0 | 63.0 |
| 24 | Ethyl methyl ketone | 23.2 | 35.2 |

TABLE 3-continued

| Product crosslinked with sorbitol diglycidyl ether | | Absorption value in completely demineralized water (ml/g) | |
|---|---|---|---|
| Example | Solvent | 0.5 minute | 10 minutes |
| 25 | 2-ethylhexan-1-ol | 30.2 | 59.4 |
| 26 | Methanol | 33.0 | 61.4 |
| 27 | Methyl acetate | 27.6 | 56.9 |

TABLE 4

| | Absorption values in synthetic urine (ml/g) | |
|---|---|---|
| Example | 0.5 minute | 10 minutes |
| 9 | 16.6 | 25.4 |
| 19 | 16.2 | 27.5 |
| 22 | 13.0 | 24.9 |

TABLE 5

| | Biological degradation (%) | | | |
|---|---|---|---|---|
| Days | Sodium Benzoate | Example 5 | Example 19 | Example 22 |
| 3 | 30.3 | 3.7 | 3.4 | 3.5 |
| 5 | 52.4 | 30.0 | 21.0 | 19.1 |
| 7 | 58.9 | 44.4 | 32.5 | 29.6 |
| 10 | 65.8 | 53.6 | 42.7 | 37.9 |
| 14 | 71.3 | 60.5 | 50.0 | 52.9 |
| 19 | 73.9 | 64.3 | 53.6 | 55.8 |
| 24 | 76.4 | 70.5 | 57.2 | 58.7 |
| 28 | 78.6 | 72.8 | 60.2 | 60.4 |
| 32 | 79.3 | 75.2 | 62.3 | 61.1 |

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method of preparing a chitosan super-absorbent comprising:
   reacting pulverized chitosan suspended as a powder in an organic solvent with an acid, wherein water is present in an amount of 1–80%, based on the amount of chitosan, and wherein the water content is present in a maximum amount of about 10% by weight based on the weight of the organic solvent; and
   isolating the solid super-absorbent chitosan-acid reaction product.

2. The method according to claim 1, wherein the weight ratio of solvent to chitosan is 1:1 to 100:1.

3. The method according to claim 2, wherein said weight ratio ranges from 5:1 to 20:1.

4. The method according to claim 1, wherein the amount of acid reactant ranges from 1 to 30 mmol/g of chitosan.

5. The method of claim 4, wherein said amount of acid ranges from 2 to 10 mmol/g chitosan.

6. The method according to claim 1, which further comprises reacting the pulverized chitosan with a crosslinking agent.

7. The method according to claim 6, wherein the crosslinking of the chitosan occurs after its reaction with the acid.

8. The method according to claim 6, wherein the crosslinking of the chitosan occurs during the reaction with the acid.

9. The method according to claim 6, wherein the amount of crosslinking agent ranges from 0.0001 to 10 mmol/g of chitosan.

10. The method of claim 1, wherein said acid is a mineral acid, a sulfonic acid, a carboxylic acid of 1 to 4 carboxylic acid groups or a hydroxy carboxylic acid.

11. The method of claim 6, wherein said crosslinking agent is a dicarboxylic acid, a dianhydride, a diacid chloride, a diepoxide or a dialdehyde.

12. A method of absorbing aqueous media, comprising:
contacting an aqueous medium with the reaction product of chitosan with an acid prepared by reacting pulverized chitosan suspended as a powder in an organic solvent with an acid, wherein water is present in an amount of 1–80%, based on the amount of chitosan, and wherein the water content is present in a maximum amount of about 10% by weight based on the weight of the organic solvent; and isolating the solid chitosan-acid reaction product.

* * * * *